US007825133B2

(12) United States Patent  (10) Patent No.: US 7,825,133 B2
Yi  (45) Date of Patent: Nov. 2, 2010

(54) DERIVATIVES OF PYRIDONE AND THE USE OF THEM

(75) Inventor: Xianghui Yi, Shanghai (CN)

(73) Assignee: Shanghai Genomics, Inc., Shanghai (CN)

( * ) Notice: Subject to any disclaimer, the term of this patent is extended or adjusted under 35 U.S.C. 154(b) by 313 days.

(21) Appl. No.: 10/579,288

(22) PCT Filed: Nov. 14, 2003

(86) PCT No.: PCT/CN03/00968

§ 371 (c)(1),
(2), (4) Date: May 15, 2006

(87) PCT Pub. No.: WO2005/047256

PCT Pub. Date: May 26, 2005

(65) Prior Publication Data

US 2007/0049624 A1  Mar. 1, 2007

(51) Int. Cl.
A01N 43/40 (2006.01)
A61K 31/445 (2006.01)
(52) U.S. Cl. ........................ 514/315; 514/327
(58) Field of Classification Search ............. 514/315, 514/327
See application file for complete search history.

(56) References Cited

U.S. PATENT DOCUMENTS

| 3,839,346 | A | * | 10/1974 | Gadekar | 546/249 |
| 4,866,078 | A | | 9/1989 | Perrior et al. | |
| 5,039,807 | A | | 8/1991 | Perrior et al. | |
| 5,310,562 | A | | 5/1994 | Margolin | |
| 5,716,632 | A | * | 2/1998 | Margolin | 424/423 |
| 5,789,426 | A | | 8/1998 | Hanauske-Abel et al. | |
| 5,939,439 | A | | 8/1999 | Anthony et al. | |
| 5,962,478 | A | | 10/1999 | Margolin | |
| 6,048,823 | A | | 4/2000 | Yamaguchi et al. | |
| 6,090,822 | A | | 7/2000 | Margolin | |
| 6,265,349 | B1 | | 7/2001 | Yamaguchi et al. | |
| 6,294,350 | B1 | | 9/2001 | Peterson | |
| 6,300,349 | B1 | | 10/2001 | Margolin | |
| 6,492,395 | B1 | | 12/2002 | Scheiwe et al. | |
| 6,956,044 | B1 | | 10/2005 | Margolin | |
| 7,067,540 | B2 | | 6/2006 | Devadas et al. | |
| 2003/0216257 | A1 | | 11/2003 | Sagasser et al. | |
| 2004/0058964 | A1 | | 3/2004 | Devadas et al. | |
| 2006/0039931 | A1 | | 2/2006 | Scheiwe | |

(Continued)

FOREIGN PATENT DOCUMENTS

CN  1386737  12/2002

(Continued)

OTHER PUBLICATIONS

Ansel et al, Pharmaceutical dosage forms and drug delivery systems, Seventh edition, pp. 87-92, Copyright 1999.*

(Continued)

*Primary Examiner*—Ardin Marschel
*Assistant Examiner*—Savitha Rao
(74) *Attorney, Agent, or Firm*—Wilson Sonsini Goodrich & Rosati

(57) ABSTRACT

The present invention provides N-substituted-2(1H) pyridones or the pharmaceutical acceptable salts thereof, and the pharmaceutical preparations containing the compounds. The compounds of the present invention can be used to treat various fibrotic diseases effectively, e.g., hepatic fibrosis.

17 Claims, 3 Drawing Sheets

U.S. PATENT DOCUMENTS

| | | |
|---|---|---|
| 2006/0100249 A1 | 5/2006 | Smith |
| 2006/0110358 A1 | 5/2006 | Hsu |
| 2006/0167064 A1 | 7/2006 | Seth |
| 2006/0211694 A1 | 9/2006 | Devadas et al. |
| 2006/0276510 A1 | 12/2006 | Abu-Shakra et al. |
| 2006/0279709 A1 | 12/2006 | Yamamoto |

FOREIGN PATENT DOCUMENTS

| | | |
|---|---|---|
| EP | 0 458 861 B1 | 3/1996 |
| EP | 1 138 329 A2 | 10/2001 |
| EP | 0 383 591 B1 | 11/2001 |
| EP | 0 702 551 B1 | 9/2002 |
| EP | 1 069 898 B1 | 5/2004 |
| EP | 1 261 338 B1 | 6/2006 |
| WO | WO 97/41830 A1 | 11/1997 |
| WO | WO 00/44381 | 8/2000 |
| WO | WO 01/58448 A1 | 8/2001 |
| WO | WO 2005/047256 A1 | 5/2005 |
| WO | WO 2006/004100 A1 | 1/2006 |
| WO | WO 2006/108354 A1 | 10/2006 |
| WO | WO 2006/109876 A1 | 10/2006 |

OTHER PUBLICATIONS

Worbel et al, J. Med. Chem., 1989, vol. 32(11): 2493-3000, abstract.*

Patani et al (Chemical Reviews, 1996, vol. 96 (8), pp. 3147-3176.*

Chin Pharm J. vol. 37, No. 4, Apr. 2002, Pu Han-Lin et al., "Protective effects of 2-ethyl3-hydroxy-6-phenylthio-4-(1H)-pyridinone on injured primary cultured rat hepatocytes induced by $CCl_4$," pp. 267-271.

Pu et al., "Protective effects of 2-ethyl-3-hydroxy-6-phenylthio-4-(1H)-pyridinone on injured primary cultured rat hepatocytes induced by $CCl_4$," 2002, Chin Pharm J. vol. 37(4): 267-271 (in Chinese with English abstract).

* cited by examiner

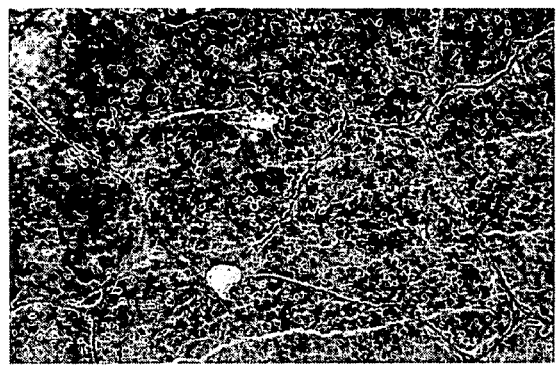 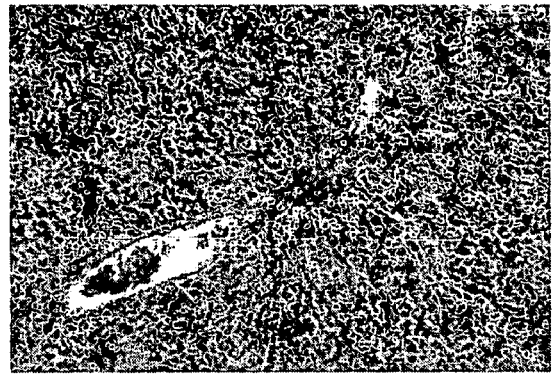
Fig. 8　　　　　　　　　　　Fig. 9
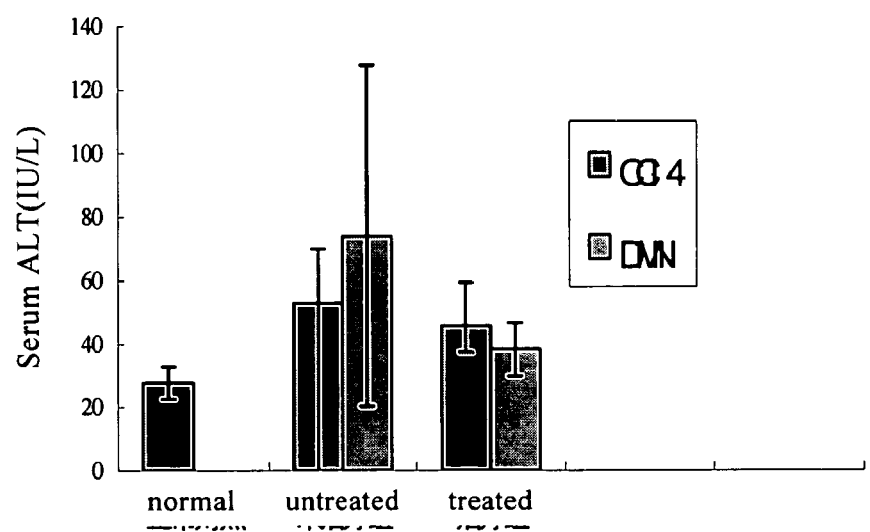
Fig. 10

DERIVATIVES OF PYRIDONE AND THE USE OF THEM

CROSS-REFERENCE TO RELATED APPLICATION

This Application is a Section 371 National Stage Application of International Application No. PCT/CN2003/000968, filed 14 Nov. 2003 and published as WO 2005/047256 A1 on 26 May 2005, the subject matter of which are hereby incorporated by reference in its entirety.

TECHNICAL FIELD

The present invention relates to the pharmaceutical field, and in particular, to pyridone derivatives for treating fibrosis, the preparation and use of the same.

BACKGROUND ART

Fibrosis is a widespread disease involving various organs of a human body. It harms the function of organs mainly by way of the excessive production and deposition of collagen proteins resulting from inflammatory reactions. Fibrosis occurs in various tissues and organs of human body, such as cardiac muscle, liver, lung, kidney and skin. Once fibrosis happens, the function of this organ and even the whole body will usually be extremely damaged. For example, scar tissue proliferation caused by skin wound not only affects the appearance but also affects the movement of limbs in severe cased; the fibrosis of cardiac muscle caused by coronary heart disease is a key factor of heart failure; kidney fibrosis caused by chronic glomerular nephritis and pyelonephritis is responsible for over 90% uraemia caused by renal failure; lung fibrosis caused by multiple lung pathologic changes often results in death due to respiratory failure. One of the main symptoms of non-typical pneumonia breaking out in the year of 2003 is fibrosis of lung tissue.

Liver fibrosis is the common pathologic basis of the progress of chronic liver diseases. Various chronic damages lead to degeneration and necrosis of hepatocytes, and the abnormal proliferation and excessive deposition of fibrous connective tissue. The proliferative and overdeposited fibrous connective tissue encapsulates the regenerated hepatocytes to form "pseudo-lobule" which destroys the original structure of the liver and finally leads to the formation of nodule, sclerosis and cirrhosis, with the hepatic function impaired or even completely eliminated. Each year in the world, up to almost one million people die from liver cirrhosis, and there is still an upward trend. Cirrhosis is among the main reasons of death in the European countries, America, Japan and China, only next to cerebrovascular accident, angiocardiopathy and maglignant tumor.

Many chronic liver diseases, such as chronic viral hepatitis, chronic alcoholism, cholestasis, dysmetabolism disorder of congenital enzyme defects, and long-term contact with toxin and drugs, can cause liver fibrosis. Among them, chronic viral hepatitis is the most common cause. The Hepatitis B is very popular in China. HBV antigen can be detected in about 76% of liver tissue with cirrhosis. A scientific research has shown that there are over 500 million carriers of Hepatitis B virus around the world. In China, 600 million people have been infected with Hepatitis B virus once, about 120 million people are carriers of Hepatitis B virus, and over 30 million patients suffer from chronic Hepatitis B, among which more than 20-30% are expected to develop into cirrhosis in 5-10 years, while about 20% of people with cirrhosis may develop into primary liver cancer. In view of the linkage relationship between Hepatitis B virus, cirrhosis and liver cancer, there are up to 400,000 people in China who die from cirrhosis after Hepatitis B infection and the liver cancer. It is of great significance to effectively prevent liver fibrosis and cirrhosis of the patients with a liver disease.

Although antivirus and anti-inflammation are the basis of Hepatitis B treatment, in fact, the conditions of most of the patients infected with Hepatitis B virus will have a chronically progressive development. Antivirus alone can not prevent the progression of the disease. A large portion of these patients will inevitably develop cirrhosis or liver failure gradually, which is the later stage of the chronic liver disease and is a result of liver fibrosis induced by long-term hepatocyte necrosis. If the condition can not be controlled, it will continuously develop to damage various organs. Such damages mainly include severe complications such as impaired liver function, portal hypertension, hemorrhage of digestive tract, hepatic encephalopathy and concurrent infections. Due to the lack of an effective therapeutic method available at present, the mortality is very high. In areas where liver diseases are popular, such as China and Southeastern Asia, hundreds of thousands young people lose their lives as a result of these complications every year.

At present it is believed that the cirrhosis lesion is irreversible. Even if the primary cause is eliminated, the condition will still develop and deteriorate. Liver fibrosis is a primary stage in the development of various chronic liver diseases into cirrhosis, and it is also the common pathologic basis of cirrhosis. From the viewpoint of treatment, this stage is reversible. It can be recovered to the original state upon treatment. Therefore, it is a key and breakthrough point to cure most of the refractory liver diseases by blocking and reversing liver fibrosis as soon as possible before it develops into cirrhosis.

The development of anti-fibrotic medicaments typically starts from the following aspects including inhibiting synthesis of collagen, inhibiting the expression of collagen mRNA, enhancing the degradation of collagen, and inhibiting the immune response of the organism. Now some medicaments, such as interferon, colchine, corticosterone hormone, malotiate, have been used in the research of anti-fibrosis. However, these medicaments have the disadvantages of high toxicity and side effects and high price, which limit their clinical application. At present, there is not an effective therapeutic means for fibrosis.

U.S. Pat. No. 5,789,426 discloses a method for treating fibrosis disease by administration of a protein hydroxylation inhibitor, wherein the inhibitor is a N-substituted hydroxyl pyridone derivative.

U.S. Pat. No. 6,090,822 discloses the use of N-substituted 2(1H) pyridone or N-substituted 3(1H) pyridone for treating the diseases caused by cytokines.

WO00/44381 discloses the use of N-substituted 2(1H) pyridone or N-substituted 3(1H) pyridone for treating cancers, such as lymphomas and leukemia, etc.

EP 1138329 discloses the use of 5-methyl-1-phenyl-2-(1H)-pyridone for treating fibrotic injuries.

Pirfenidone (PF) is a small molecule compound initially invented in the early 1980s. It has the effects of inhibiting the synthesis of collagen, decreasing the secretion of cytokines, and preventing the proliferation of fibroblast. The specific target gene of this agent is still unclear. Since then, it has been used to successfully inhibit the fibrosis of heart, kidney, lung and vascular inner wall in various animal models. This agent is being in Stage III clinical trial for treating idiopathic fibrosis of the lung (IPF) in America. However, the inhibitory activity of PF is not sufficiently satisfying.

Anti-fibrotic medicaments have a large demand in the market. It is estimated that 45% of causes of deaths in America can be attributed to physiological disorder of fibrotic proliferation, for example, liver fibrosis/cirrhosis, kidney fibrosis, heart fibrosis and lung fibrosis. Therefore, there is an urgent need in the art to develop novel compounds and medicaments for the effective inhibition of various fibrosis.

SUMMARY OF INVENTION

The objective of the present invention is to provide a compound for the effective inhibition of various fibrosis, and the use thereof.

In the first aspect of the present invention, it provides the compound of formula I or the pharmaceutically acceptable salts thereof:

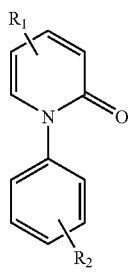

(I)

wherein, $R_1$ is methyl, ethyl or trifluoromethyl at position 3, 4, 5 or 6;

$R_2$ is hydroxyl, sulfydryl, methylthio group, ethylthio group at position 2, 3 or 4.

In another preferred embodiment, $R_1$ is methyl, and $R_2$ is hydroxyl. More preferably, $R_1$ is methyl at position 5, and $R_2$ is hydroxyl at position 4.

In the second aspect of the present invention, it provides a pharmaceutical composition, comprising a pharmaceutically acceptable carrier and a safe and effective amount of the compound of formula I or the pharmaceutically acceptable salts thereof.

Typically, the pharmaceutical composition comprises 0.01-99%, preferably 0.1-90%, still more preferably 1-80% of the compound of formula I or the pharmaceutically acceptable salts thereof, on the basis of the total weight of the composition.

In another preferred embodiment, the dosage form of the pharmaceutical composition is tablet, capsule, ampule, or pill.

In the third aspect of the present invention, it provides a method for producing the compound of formula I, comprising the steps of:

(a) in the presence of copper powder and anhydrous alkaline earth metal carbonate (e.g. potassium carbonate, sodium carbonate), reacting the compounds of formula II and formula III (in a molar ratio of about 0.8-1.2:0.8-1.2) at 160-200° C., thereby producing the compound of formula Ia;

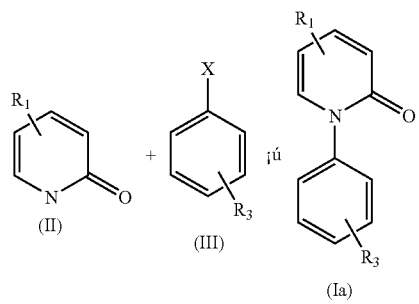

wherein $R_1$ is methyl, ethyl or trifluoromethyl at position 3, 4, 5 or 6, $R_3$ is —$OCH_3$, —$SCH_3$, —$OC_2H_5$ or —$SC_2H_5$ at position 2, 3 or 4, X is Cl, Br or I;

(b) reacting the compound of formula Ia with $BBr_3$ in an inert solvent (for example, dichloromethane, carbon tetrachloride, benzene, methyl benzene, cyclohexane, or a mixture thereof) at −10° C. to 15° C. (more preferably −5°C. to 10° C.), thereby producing the compound of formula I:

wherein, $R_1$ and $R_3$ are defined as above, $R_2$ is —OH or —SH.

In the fourth aspect of the present invention, it provides a method for producing a pharmaceutical composition, comprising the steps of: mixing the compound of formula I or the pharmaceutically acceptable salts thereof and a pharmaceutically acceptable carrier to produce a pharmaceutical composition comprising 0.01-99 wt % of the compound of formula I, on the basis of the total weight.

In the fifth aspect of the present invention, it provides the use of the compound of formula I or the pharmaceutically acceptable salts thereof in the manufacture of a medicament for preventing fibrosis.

The present invention also provides a method for treating fibrosis diseases, comprising the administration of a safe and effective amount of the compound of formula I or the pharmaceutically acceptable salts thereof to a subject in need thereof.

DESCRIPTION OF THE DRAWINGS

FIG. 8 is the Masson staining of the $CCl_4$ model group at week 4, 2.5×10.

FIG. 9 is the Masson staining of the $CCl_4$+F351 treatment group at week 4, 2.5×10.

FIG. 10 shows the level of alanine aminotransferase (ALT) in the serum at week 4 after the F351 treatment.

MODE OF CARRYING OUT THE INVENTION

Figure 1:
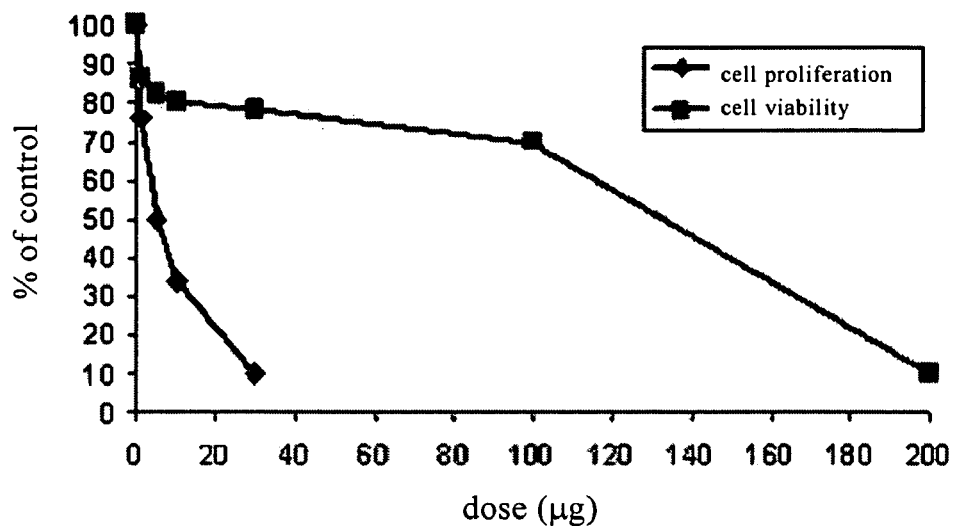
FIG. 1 shows that F351 inhibits the proliferation and cell viability of the fibroblast.

Through analyzing the structures of various kinds of known small molecule compounds for inhibiting inflammatory reactions, including Pirfenidone, the inventor of the present invention designed and synthesized a series of brand new compounds, and furthermore, screened a kind of pyridone derivatives, which significantly inhibit the division and proliferation of the fibroblast cultured in vitro without observable toxicity to cells.

As used herein, the term "the compound of the present invention", "the compound of formula I", which can be used interchangeably, means the compound having the structural formula I or the pharmaceutical acceptable salts thereof, wherein the groups are defined as above.

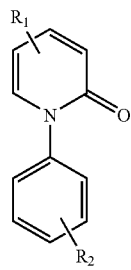

(I)

A particularly preferred compound is 5-methyl-1-(4-hydroxylphenyl)-2-(1H)-pyridone, which is called F351.

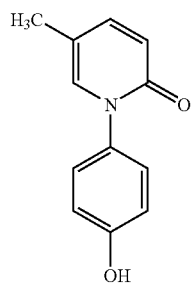

The compounds of the present invention such as F351 are characterized by their small molecular weight (about 200), high water solubility, oral administration, and easy synthesis. The compound can inhibit the proliferation of the fibroblast in cell tissues, and thereby dramatically reduce the synthesis of collagen. Results of the animal experiments have shown that F351 has a potent anti-fibrotic effect, and furthermore, it can significantly reduce hepatocyte necrosis in addition to its effect of anti-fibrosis of liver. It can be used in the treatment of diseases including acute viral hepatitis to reduce hepatocyte damage. Experiments have shown that this compound is very safe to cell tissues and animals, even in a high concentration.

The compound of the present invention may also be used to treat various fibrosis diseases and inflammations leading to fibrosis, for example, the fibrosis or fibrous tumor of the tissues such as cardiac muscle, liver, lung, kidney, blood vessel and skin. Exemplary examples include, but not limited to, liver fibrosis, cirrhosis, liver necrosis, chronic obstructive pulmonary disease, lung fibrosis, cardiac muscle fibrosis, kidney fibrosis, blood vessel fibrosis, skin scar, etc.

The compounds of the present invention also include the salts derived from pharmaceutically or physiologically acceptable acids or bases. Such salts include, but not limited to, the salts derived from the following inorganic acids: hydrochloric acid, sulphuric acid, nitric acid, phosphoric acid, and those derived from the following organic acids: acetic acid, ethanedioic acid, butanedioic acid, tartaric acid, methane sulfonic acid and maleic acid. Other salts include those formed with alkali metal or alkaline earth metal (such as sodium, potassium, calcium or magnesium), in the form of esters, carbamates or other conventional "pro-drugs" (which can be transformed in vivo into active ingredients).

The present invention also encompasses a pharmaceutical composition and a therapeutic method, comprising the administration of a pharmaceutically effective amount of the compound of formula I to mammals.

When the compound of the present invention is used in the above-mentioned application, it can be mixed with one or more pharmaceutically acceptable carriers or excipients, such as solvent, diluents, etc. It can be orally administered in the following dosage forms: tablets, pellets, capsules, dispensable powders, particles or suspensions (containing, e.g. about 0.05-5% suspending agent), syrup (containing, e.g. about 10-50% saccharide), and elixirs (containing, about 20-50% ethanol). Alternatively, it can be administered by external use in the form of ointment, gel, drug-containing rubber cement, etc. Alternatively, it can be administered parenterally in the form of sterile injectable solution or suspension (containing about 0.05-5% suspending agent in isotonic media). For example, these pharmaceutical preparations may contain about 0.01 -99 wt %, more preferably about 0.1-90 wt % active ingredients mixed with carriers.

The effective dose of the active ingredients used may vary with the compound used, the administration mode and the severity of the disease to be treated. However, typically, a desirable result can be achieved when the compound of the present invention is administered at a dose of about 0.25-1000 mg/kg animal body weight per day. More preferably, it is administered in 2-4 separated dosages per day, or in the form of slow release. For most of the large mammals, the total dose per day is about 1-100 mg/kg, more preferably about 2-80mg/kg. The dosage form suitable for inner use comprises about 0.25-500 mg active compound sufficiently mixed with a solid or liquid pharmaceutically acceptable carrier. The dosage may be adjusted to provide the best treatment response. For example, upon urgent requirement of the condition to be treated, several separate dosages per day may be administered, or the dosage may be reduced in proportion.

These active compounds may be administered orally, intravenously, intramuscularly or subcutaneously. Solid carriers include starch, lactin, dicalcium phosphate, microcrystalline cellulose, sucrose and white bole, while liquid carriers include sterile water, polyethylene glycol, nonionic surfactant and edible oil (e.g. corn oil, peanut oil and teel oil), as long as these carriers are suitable for the properties of the active ingredients and the desired specific administration means. Advantageously, the adjuvants commonly used in the production of a pharmaceutical composition, for example, a flavoring agent, colorant, preservative and antioxidant such as vitamin E, vitamin C, BHT and BHA, are also included.

From a point of view of easy production and administration, the preferred pharmaceutical composition is a solid composition, especially tablets and capsules filled with solid or liquid. Oral administration of the compound is preferred.

These active compounds may be administered parenterally or intraperitoneally. These active compounds (as free bases or pharmaceutically acceptable salts) may be formulated into solutions or suspensions in water suitably mixed with surfactant (e.g. hydroxypropyl cellulose, polyvinyl pyrrolidone). Dispersion can also be prepared from the mixture of these active compounds in glycerin, liquid, polyethylene glycol and oil. In the normal condition of storage and usage, these preparations contain preservatives to prevent the growth of microorganisms.

The pharmaceutical forms suitable for injection include sterile water or dispersion and sterile powder (used for the temporary preparation of sterile injectable solutions or dispersions ). In all the cases, these forms must be sterile, and they must be fluidic to allow the discharge of the fluid from the injection syringe. These forms must be stable in the condition of production and storage, and must be able to prevent the contamination of microorganisms (such as bacteria and fungi). The carriers may be solvents or dispersion media, including, for example, water, alcohol (such as glycerin, propylene glycol and liquid polyethylene glycol), the suitable mixture thereof, and plant oil.

Additionally, the compound of the present invention may be used in combination with other agents of treating fibrosis, such as α-interferon, β-interferon, γ-interferon, cortical hormone and methotrexate.

The main advantages of the present invention include (a) a good effect on inhibiting fibrosis; (b) few side effect, and (c) the capability to inhibit inflammation and tissue necrosis leading to fibrosis.

The invention is further illustrated by the following examples. These examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Synthesis and Characterization of F351

Step 1: Synthesis of 5-methylpyridone

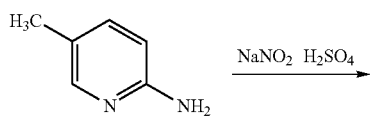

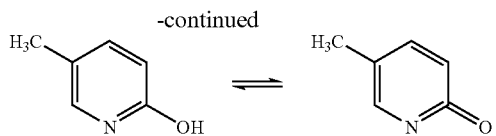

1. 2-amino-methylpyridine (30 g, 0.278 mol) was dissolved in 800 ml 6.3% sulphuric acid.
2. Sodium nitrite (36 g, 0.522 mol) was dissolved in 100 ml water, then added dropwise into the solution at ambient temperature. This reaction was an exothermic reaction and gave out a large amount of gas.
3. The solution was stirred for 2 hours after completion of the addition, then refluxed in an increasing temperature for 4 hours. The light yellow solution became black. It was naturally cooled down to the ambient temperature.
4. In a condition of decreasing the temperature by ice bath, sodium carbonate was added to the solution for neutralization. Then the pH value was adjusted to 8. This reaction was an exothermic reaction and gave out a large amount of gas.
5. The reaction mixture was concentrated by distillation under reduced pressure at 65° C. The concentrated solution was extracted by dichloromethane. The extraction was repeated several times until the blot plate of the organic phase did not show product blot. The extraction solution was dried with anhydrous sodium sulfate, and dried by spinning to give the crude product.
6. The crude product was recrystallised with ether-dichloromethane (10/1) to produce 27.3 g (0.25 mol) of the title compound, as light yellow solid. The yield was 89%.

Step 2: Synthesis of 5-methyl-1-(4-methoxylphenyl)-2-(1H)-pyridone

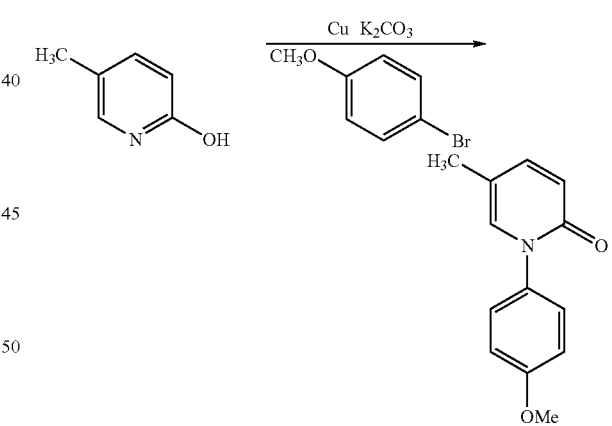

1. Para-bromoanisole (115 ml), 5-methylpyridone (26 g), anhydrous potassium carbonate (36.4 g) and copper powder (520 mg) were stirred at 180° C. for 18 hrs, then cooled down to the ambient temperature.
2. The mixture was filtered with Celite, then eluted with dichloromethane to produce the concentrated solution.
3. The concentrated solution was distilled under reduced pressure. Then the solvent of para-bromoanisole was removed by distillation. The residue was the desired crude product.
4. The crude product was recrystallised with solvent ethyl acetate. Ether was used as the eluting reagent. 28 g title compound was obtained. The yield was 58%.

Step 3: Synthesis of 5-methyl-1-(4-hydroxylphenyl)-2-(1H)-pyridone

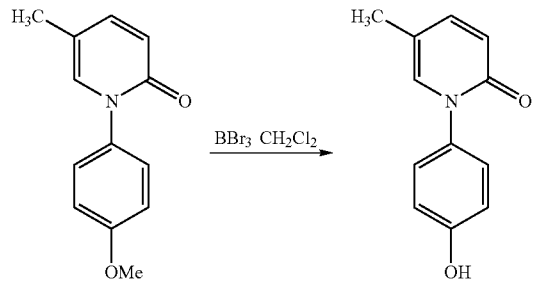

1. 100 g 5-methyl-1-(4-methoxylphenyl)-2-(1H)-pyridone was dissolved in 2 L dichloromethane, and boron tribromide (1000 ml, 1 M, in dichloromethane) was gradually (dropwise) added into the solution at 0° C. in ice bath, with the temperature not over 5° C. When the ⅔ of boron tribromide solution was added, the solid precipitated. After the completion of dropwise addition, the solution was stirred for 1 hr at 0° C.

2. 400 ml ether was added dropwise into the solution to form a complex compound of ether and boron tribromide. It was an exothermic reaction. The speed of dropwise addition was controlled to maintain the temperature of the system not exceeding 10° C. After the completion of addition, the solution was stirred for 40 mins at 0° C.

3. The reaction was quenched by adding water. It was an exothermic reaction. The speed of addition was controlled to maintain the temperature of the system not exceeding 15° C.

4. The solid was collected by vacuum filtration.

5. The solid was recrystallised with solvent ethanol to give 40 g title compound, which was named as F351. The yield was 40%.

$^1$H NMR (CDCl$_3$, ppm): 2.16(s, 3H); 6.58(d, 1H); 6.92(d, 2H); 7.19(d, 2H); 7.39(s, 1H); 7.51(dd, 1H)

$^{13}$C NMR (ppm): 16.9; 118.3; 121.0; 127.8; 129.8; 130.5; 137.5; 142.5; 145.4

EXAMPLE 2

F351 Inhibited the Proliferation of Fibroblast Cultured in vitro

The inhibitory effect of F351 on the proliferation of fibroblast cultured in vitro was tested using the following method. F351 was dissolved in 0.5% DMSO. The fibroblast was treated with F351 of different amount (FIG. 1 and FIG. 2) for 5 days. The agent was refreshed once every 48 hrs. Pirfenidone was used in parallel experiments in order to compare the effects of these two agents.

MTT assay: 100 ml cell suspension was added into each well of a 96-well plate, 4 parallel wells per group. The concentration of the agent and the culture time remained unchanged. Then 10 μL 5 g/L MTT (3-(4,5-dimethylthiazol-2-yl)-2,5-diphenyltetrazolium bromide) was added to each well for another 4 hrs of culture. 100 uL DMSO was added to each well. Gently vortex to make a uniform mixture. After about 10 mins, OD values at 570 nm and 630 nm were measured by an enzyme linked immune detector (BIO RAD 550). The cell viability rate was calculated in accordance with the following formula:

Viability rate=[(experimental well OD$_{570}$−experimental well OD$_{630}$)/(control well OD$_{570}$−control well OD$_{630}$)]×100%

Inhibition rate (or proliferation rate)=100%−viability rate

Figure 2:
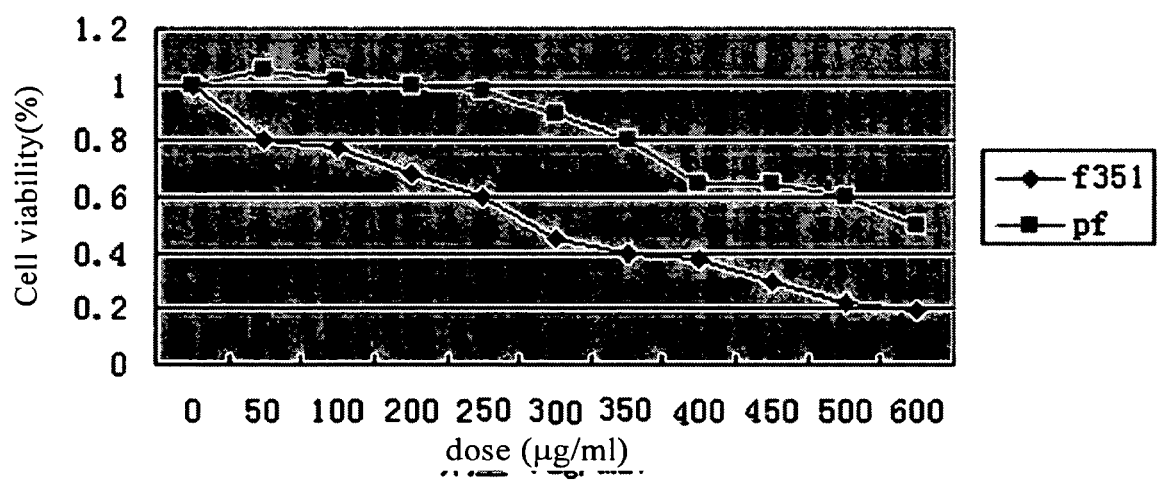
FIG. 2 shows that the activity of F351 for inhibiting the fibroblast viability is higher than that of the Pirfenidone control, indicating that F351 significantly inhibits the collagen synthesis.

The results showed that the inhibitory effect of F351 on the fibroblast was more significant than that of Pirfenidone (FIG. 1 and FIG. 2).

EXAMPLE 3

F351 Showed Obvious Anti-fibrotic Effect in a Liver Fibrosis Model, and it also Reduced the Hepatocyte Necrosis A rat liver fibrosis model was established by induction with CCl$_4$ and DMN (dimethyl nitrosamine)) respectively, and treated with F351 for 4 weeks, 8 weeks. The livers of the animal were harvested to observe the pathologic results. The method was as follows:

(a) Generating a carbon tetrachloride model (injected intraperitoneally with 40% CCl$_4$ mixed with oil, 0.4 ml/100 g, twice per week, for 4 continuous weeks) and a dimethyl nitrosamine liver fibrosis model (injected intraperitoneally with 1% DMN, 10 mg/Kg, twice per week, for 8 continuous weeks).

(b) The animals of these two models were intragastrically administered with F351 from the 0 day of the model establishment, with the dose at 250 mg/Kg, once per day, for 4 or 8 continuous weeks.

Figure 3:
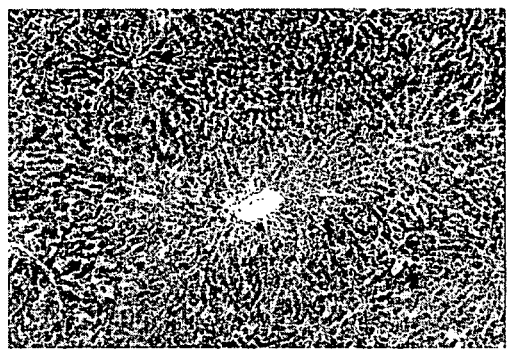
FIG. 3 shows a Masson triple staining of a normal rat liver tissue, 2.5×10.
Figure 4:
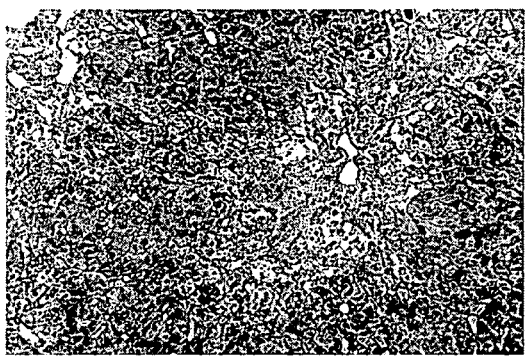
FIG. 4 shows a Masson triple staining of the DMN model group at week 4, 2.5×12.5. After hemorrhage and necrosis, collagen deposit and peri-sinus fibrosis are observed.
Figure 5:
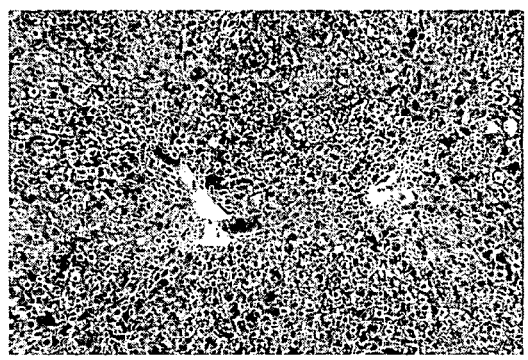
FIG. 5 shows a Masson triple staining of the DMN+F351 treatment group at week 4, 2.5×16. A small amount of collagen deposition and formation of fibrous septum after necrosis are observed around the central veins.

Results:

(a) DMN Model:

Compared with the normal rats (FIG. 3), hepatocyte necrosis around the central veins, hemorrhage and collagen deposition, fibrosis around the sinus were obviously observed in the model group at week 4; the lesion in the F351 treatment group was significantly reduced (P<0.001), and only a small amount of collagen deposition and formation of fibrous septum after necrosis were observed around the central veins (FIG. 4 and FIG. 5).

Figure 6:
FIG. 6 shows the HE staining of the DMN model group at week 8, 2.5×20. Fibrosis around the central veins, deposition of the ferri-containing xanthematin and the accompanying fresh hemorrhage are observed.
Figure 7:
FIG. 7 shows the HE staining of the DMN+F351 treatment group at week 8, 2.5×16. Necrosis around the central veins is little, the dimension of fibrosis is smaller, and the fibrosis around the sinus are more than those seen in the normal.

At week 8, in the model group, the cells around the central veins fiberized after necrosis; local lesion was infiltrated by inflammatory cells; there was fresh hemorrhage and necrosis; fibrosis occurred around the sinus and the fibrous septum formed. While in the F351 treatment group, the pathologic results showed that the necrosis dimension around the central veins was small, the fibrosis dimension was small and the boundary of the fibrosis was clear; the fibrosis around the sinus is more than that seen in the normal, but obviously better than the control group (FIG. 6 and FIG. 7).

These results showed that F351 had an obvious therapeutic effect on hepatocyte inflammation and necrosis caused by DMN, and it could inhibit the hepatocyte necrosis and effectively block the progress of liver fibrosis caused by DMN (P<0.001). The hepatocyte necrosis was significantly reduced upon F351 treatment, indicating that F351 had an inhibitory effect on the hepatocyte necrosis. Therefore, F351 could be used to treat diseases such as toxic hepatitis.

(b) CCl$_4$ Model:

The experiment was conducted for 4 weeks. The pathologic score of the model group was at the level of S4-S6, while the pathologic changes of the F351 group was obviously reduced, and the fibrosis dimension around the central veins and around the sinus was obviously reduced (4 weeks, P=0.001) (FIGS. 8 and 9).

These results showed that F351 could effectively block the progress of liver fibrosis of the rat $CCl_4$ model group.

EXAMPLE 4

The Mortality of the Rats in the Liver Fibrosis Model was Reduced After F351 Treatment The rat liver fibrosis models established by induction with $CCl_4$ and DMN were treated with F351 in the same manner in Example 3. The body weight and mortality of the rates were observed.

The result showed that the treatment with DMN or $CCl_4$ could significantly influence the body weight and mortality of the rates. After the administration of F351, as for the liver fibrosis model induced by $CCl_4$, F351 did not increase the mortality of the rats; as for the liver fibrosis model induced by DMN, F351 could significantly decrease the mortality of the animals, which was significantly distinguished from the control group (at week 4 and 8, 7 and 2 rats of the 25 rats in the control group survived, respectively, while 24 and 18 rate of the F351 treatment group survived, respectively).

EXAMPLE 5

F351 Treatment Significantly Improved the Liver Function of the Rats in the Liver Fibrosis Model The rat liver fibrosis models established by induction with $CCl_4$ and DMN were treated with F351 in the same manner in Example 3. The serum of the rats was extracted and the level of the serum transaminase was measured.

The results showed that, at week 4 of the experiment, F351 could reduce the ALT serum level in the rat with liver fibrosis induced by DMN or $CCl_4$ (the control group: 27±5.09, $CCl_4$ model group: 52±17.15, $CL_4$ model group+F351: 45±17.68; DMN model group: 74±18.25, DMN model group±F351group: 54±17.25; P<0.05) (FIG. 10). These results indicated that F351 could effectively reduce the serum transaminase level and improve the liver function.

EXAMPLE 6

| Preparation of a pharmaceutical composition containing F351 (a) Tablet | |
|---|---|
| F351 | 100-500 mg |
| polyvinyl pyrrolidone | 2-4 mg |
| silicic acid | 1 mg |
| Starch | 40-80 mg |
| magnesium stearate | 1-5 mg |
| Lactin | 5-10 mg |
| talcum powder | 5-10 mg |

F351, lactin and starch were weighted for 1000 tablets (the formulation as described above), comminuted and screened with a 80 mesh screen, respectively, mixed, and then were mixed with polyvinyl pyrrolidone and silicic acid. Then starch was added. The mixture was moistened with water, and formulated into particles with 16-18 mesh screen, dried at 60° C., granulated, mixed uniformly with talcum powder and pressed into tablets.

| (b) Parenteral solution | |
|---|---|
| F351 | 20-100 mg |
| sodium chloride | 1-5 mg |
| water for injection | To 10 ml |

According to the above formulation, F351 and sodium chloride were weighted and formulated into a solution, then poured into a 10 ml parenteral solution vial, packed after sterilization and used for injection.

| (3) Capsule | |
|---|---|
| F351 50 | 200 mg |
| polyvinyl pyrrolidone2 | 10 mg |
| starch 50 | 100 mg |
| lactin 2 | 10 mg |

The above ingredients were weighted in the amount of 1000 capsules, comminuted and screened, respectively, mixed uniformly. Then F351 was added in an increasing manner with equivalent increment, grinded completely to be uniformly dispersed, screened with a 80-mesh screen, and filled into capsules.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A pharmaceutical composition comprising:
   (a) a therapeutically-effective amount of the compound of formula I or a pharmaceutically acceptable salts thereof,

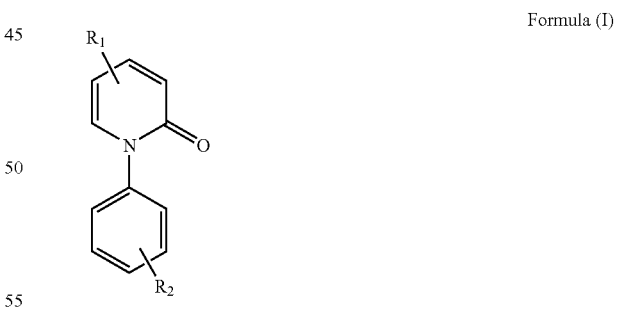

Formula (I)

wherein $R_1$ is methyl, and $R_2$ is hydroxyl; and
   (b) a pharmaceutically-acceptable excipient.

2. The pharmaceutical composition of claim 1, wherein $R_1$ is methyl at position 5, and $R_2$ is hydroxyl at position 4.

3. The pharmaceutical composition of claim 1, wherein the composition comprises 0.01-99% of the compound of formula I or the pharmaceutically acceptable salts thereof, on the basis of the total weight.

4. The pharmaceutical composition of claim 1, wherein composition is formulated as a tablet, capsule, ampule or pill.

5. The pharmaceutical composition of claim 1, wherein the pharmaceutical composition is formulated for oral, intravenous, intramuscular or subcutaneous administration.

6. The pharmaceutical composition of claim 1, wherein the pharmaceutical composition is formulated for oral administration.

7. The pharmaceutical composition of claim 1, wherein the pharmaceutical composition is formulated for external administration.

8. The pharmaceutical composition of claim 1, wherein the composition is formulated as an ointment, gel, or drug-containing rubber cement.

9. The pharmaceutical composition of claim 1, wherein the pharmaceutical composition is formulated for parenteral administration.

10. The pharmaceutical composition of claim 1, wherein the composition comprises 0.1-90% of the compound of formula I or the pharmaceutically acceptable salts thereof, on the basis of the total weight.

11. The pharmaceutical composition of claim 1, wherein the pharmaceutical composition is formulated for slow release.

12. The pharmaceutical composition of claim 1, wherein the excipient is starch, lactin, dicalcium phosphate, microcrystalline cellulose, sucrose, white bole or combinations thereof.

13. The pharmaceutical composition of claim 1, wherein the excipient is sterile water, polyethylene glycol, a nonionic surfactant, edible oil or combinations thereof.

14. The pharmaceutical composition of claim 1, further comprising an adjuvant.

15. The pharmaceutical composition of claim 1, wherein the pharmaceutical composition is formulated for administration in 2-4 separated dosages per day.

16. The pharmaceutical composition of claim 1, further comprising a flavoring agent, colorant, preservative, antioxidant, or combinations thereof.

17. The pharmaceutical composition of claim 1, further comprising vitamin E, vitamin C, butylated hydroxytoluene (BHT), butylated hydroxy anisole (BHA) or combinations thereof.

* * * * *